United States Patent
Sergio

(10) Patent No.: US 6,716,191 B2
(45) Date of Patent: Apr. 6, 2004

(54) DISPOSABLE SYRINGE

(76) Inventor: Rest Elli Sergio, Via Quarto Peperino 333 B, 00100 Rome (IT)

(*) Notice: Subject to any disclaimer, the term of this patent is extended or adjusted under 35 U.S.C. 154(b) by 0 days.

(21) Appl. No.: 10/073,299

(22) Filed: Feb. 13, 2002

(65) Prior Publication Data

US 2002/0111588 A1 Aug. 15, 2002

(30) Foreign Application Priority Data

Feb. 14, 2001 (EP) .............................. 01830095

(51) Int. Cl.[7] ................................................ A61M 5/00
(52) U.S. Cl. .................. 604/110; 604/198; 604/195
(58) Field of Search .................. 604/110, 181, 604/187, 192, 195, 198, 263

(56) References Cited

U.S. PATENT DOCUMENTS

| 5,112,316 A | * | 5/1992 | Venturini | 604/195 |
| 5,163,918 A | * | 11/1992 | Righi et al. | 604/198 |
| 5,318,538 A | * | 6/1994 | Martin | 604/110 |
| 5,338,304 A | * | 8/1994 | Adams | 604/110 |
| 5,492,536 A | * | 2/1996 | Mascia | 604/197 |
| 5,562,624 A | * | 10/1996 | Righi et al. | 604/110 |
| 5,562,626 A | * | 10/1996 | Sanpietro | 604/110 |
| 6,186,980 B1 | * | 2/2001 | Brunel | 604/110 |
| 6,319,233 B1 | * | 11/2001 | Jansen et al. | 604/192 |
| 6,319,234 B1 | | 11/2001 | Restelli et al. | 604/198 |

FOREIGN PATENT DOCUMENTS

| DE | 4314395 C1 | 12/1994 |
| EP | 0636381 A2 | 2/1995 |
| IT | WO 99/37345 | 7/1999 |
| WO | WO 9937345 A1 | 7/1999 |
| WO | WO 0064515 A1 | 11/2000 |

* cited by examiner

*Primary Examiner*—Brian L. Casler
*Assistant Examiner*—Cris L Rodriguez
(74) *Attorney, Agent, or Firm*—Rothwell, Figg, Ernst & Manbeck, PC

(57) ABSTRACT

A disposable syringe comprises a syringe body (1), a plunger (40) mounted on a stem (50) slidable inside the syringe body (1), and an injection needle (10) integral with a needle-carrier (11) engageable with the fore end (2) of the syringe body (1) or the plunger, retaining means (20, 23, 24) able to retain spring means (30) under compression being provided integrally with the syringe body (1) and engagement means (59) able to cooperate with the retaining means (23) to release the spring means (30), when the plunger (40) has reached the end of its stroke, being provided integrally with said stem (50), so that the spring means (30) can act on the stem (50) to cause retraction thereof into the retracted position.

15 Claims, 3 Drawing Sheets

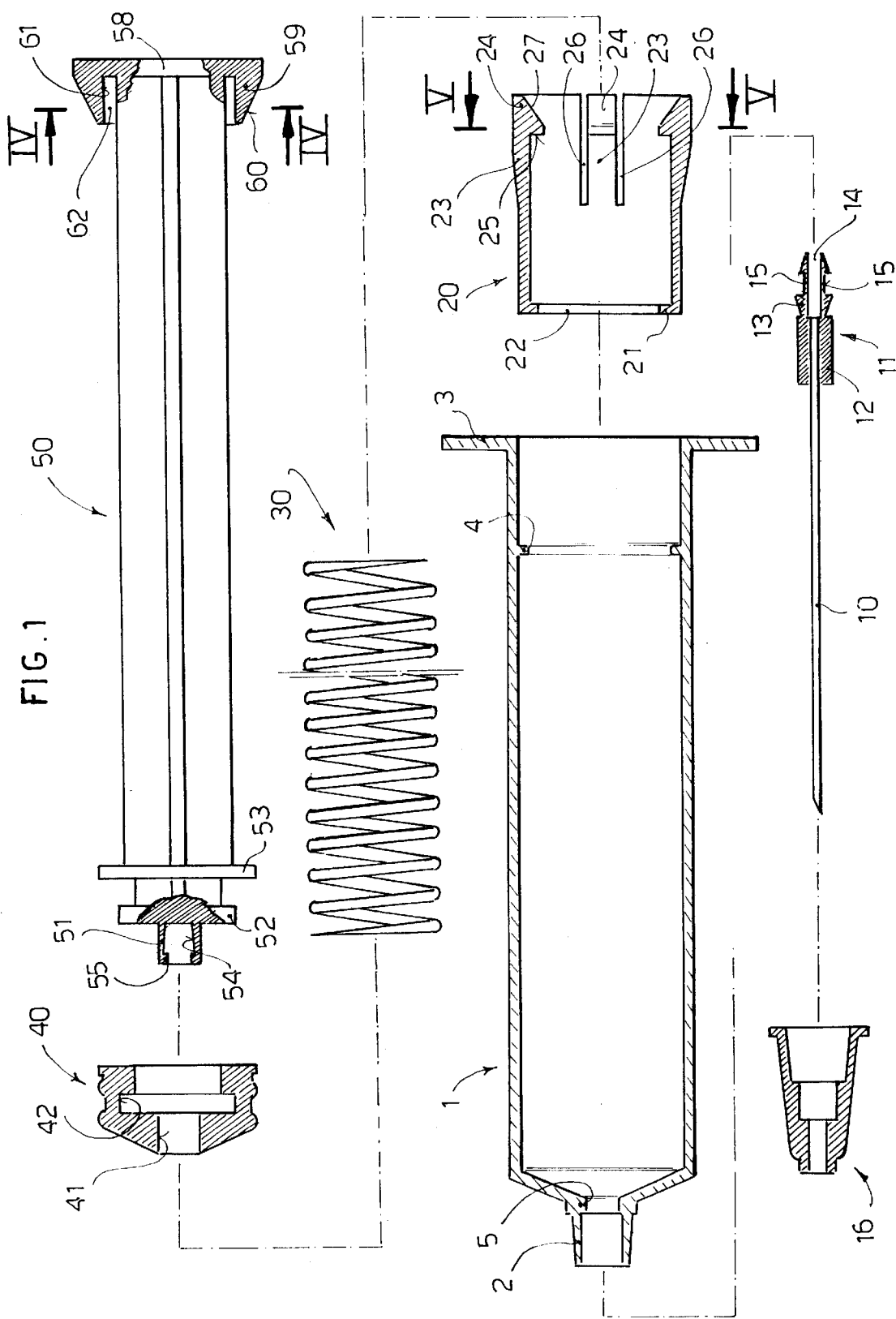

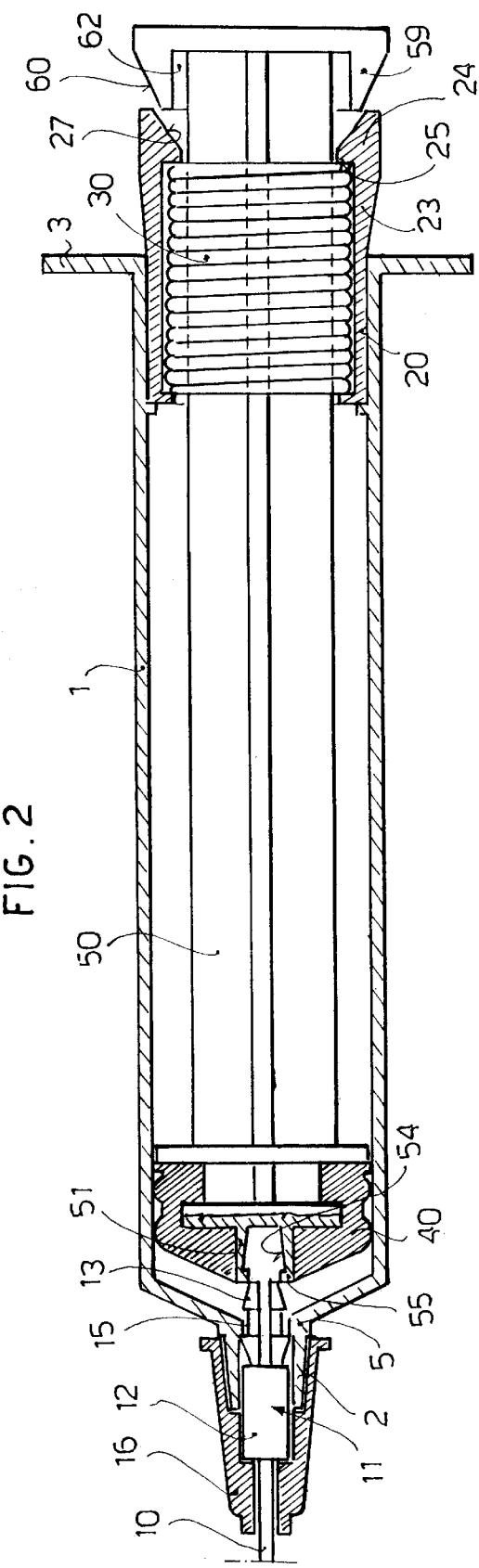

DISPOSABLE SYRINGE

DESCRIPTION

The present invention refers to an improved disposable syringe.

As is known, a syringe generally comprises a cylindrical body open at the rear to receive a plunger. An internally hollow needle is mounted at the head of the syringe body. The liquid contained in a vial is drawn into the syringe body through the needle by retracting the plunger. The liquid contained in the syringe body is injected into the patient's body through the needle by pressing on the plunger.

Because of health regulations and to avoid transmission of infectious diseases, syringes must generally be used only once and then discarded. For this reason there is a growing demand on the market for disposable syringes able to prevent re-use.

Moreover, syringes generally have drawbacks from a safety viewpoint. In fact, once the syringe has been used, the needle remains exposed at the head of the syringe body, with the risk of injury and accidental stabs.

This drawback is overcome in part by European patent EP 0636381 which describes a guard device for syringe needles. In this case, when the plunger of the syringe reaches the end of its stroke, the front end of the plunger stem captures the needle. Once the injection is completed, the user must manually retract the stem; in this manner the needle is pulled inside the syringe body by the head of the stem into the safety position which prevents accidental stabs.

This solution presents the drawback that the user, having finished the injection, can forget to carry out retraction of the stem, leaving the needle exposed and thus rendering the protection device ineffective.

Patent application PCT WO 99/37345 by the same applicant as the present application describes a disposable safety syringe which has a needle-covering sleeve mounted axially on the syringe body and slidable from a retracted position, in which it leaves the needle exposed to allow injection, to an advanced position in which it completely covers the needle, preventing re-use of the syringe and acting as a guard against accidental stabs.

Once the injection has been carried out, the sleeve is automatically brought into the extracted safety position, by means of an automatic mechanism and without any intervention by the user. Nevertheless, this solution has a certain complexity due to the provision and movement of the needle-covering sleeve.

The object of the present invention is to eliminate the drawbacks of the prior art providing an improved disposable syringe that is practical, versatile, economical and simple to make.

Another object of the present invention is to provide such a disposable syringe which is able to prevent further attempts at use.

Another object of the present invention is to provide such a disposable syringe that is extremely safe and able to prevent accidental wounds after use thereof.

These objects are achieved according to the invention with the characterstics listed in appended independent claim 1.

Advantageous embodiments of the invention are apparent from the dependent claims.

The disposable syringe according to the invention comprises a syringe body hollow on the inside and open at the front and rear, a plunger slidable inside the syringe body with an injection stroke extending from a withdrawn or retracted syringe-filling position to an advanced syringe-emptying position, and an injection needle integral with a needle-carrier that can be engaged to the front end of the syringe body or the plunger. The plunger is provided at the rear with a manually drivable stem driven out of the syringe body through the rear end thereof.

The peculiarity of the disposable syringe according to the invention is represented by the fact that, associated with said syringe body, retaining means are provided to retain spring means under compression and, integrally with said stem, engagement means are provided to cooperate with said retaining means to free said spring means when said plunger reaches the end of the injection stroke. In this manner, when the plunger reaches the end of the injection stroke, the spring means are automatically released from the retaining means and act on an abutment surface of the stem causing retraction thereof into the retracted position.

An advantageous embodiment of the invention for safety purposes, provides for the use of a needle-carrier mounted on the inside of the fore end of the syringe body and a stem which has a fore end with means able to couple with the rear end of the needle-carrier in order to retain it. In this manner, when the spring means cause retraction of the stem, the needle-carrier draws the needle with it into the syringe body chamber.

A further advantageous embodiment of the invention for safety purposes provides for use of a needle-carrier mounted integrally with the plunger. In this case the head of the syringe body provides sealing means to prevent leakage of the liquid from the annular gap formed between the outer surface of the needle and the inner surface of the cylindrical body. Moreover, at least one channel that puts the inner bore of the needle in contact with the chamber of the cylindrical body will be provided in the needle-carrier or in the plunger.

The advantages of the disposable syringe according to the invention are obvious. In fact said syringe, by causing automatic retraction of the stem of the plunger, once the injection is completed, prevents re-use thereof. Moreover, in the case of the needle-carrier being engageable with the plunger, re-entry of the plunger at the same time draws the needle into the chamber of the syringe body, avoiding accidental stabs with the utmost safety.

Further characteristics of the invention, will be made clearer by the detailed description that follows, referring to a purely exemplary and therefore non-limiting embodiment thereof, illustrated in the appended drawings, in which:

FIG. 1 is a part-sectional exploded view illustrating the disposable syringe according to the invention;

FIG. 2 is a view partially in axial section and partially broken off, illustrating the disposable syringe of FIG. 1 assembled with the plunger in the advanced position;

FIG. 3 is a broken-away part-sectional view illustrating the syringe of FIG. 1 assembled with the plunger in the retracted position;

Figure 4:
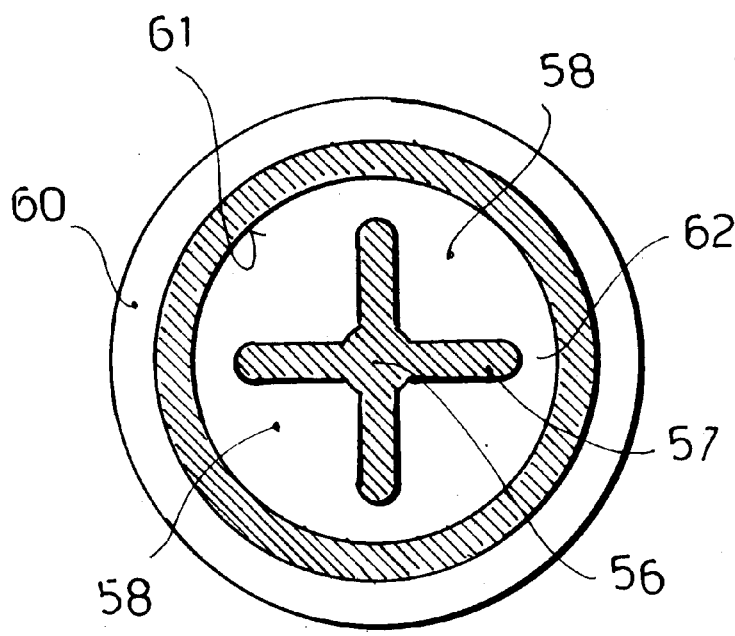
FIG. 4 is a cross-sectional view of the stem of the plunger taken along the plane IV—IV of FIG. 1.

The disposable syringe according to the invention is described with the aid of the figures.

The syringe comprises a cylindrical body 1, hollow on the inside, defining a cylindrical chamber. The rear end of the body 1 is open toward the outside and has a flange 3 that protrudes radially outward.

At a short distance from the rear end of the body 1, in the inner surface of the body 1, a projection 4 is provided defining an abutment surface that protrudes radially inward.

The fore end of the body 1 is tapered and ends with a head 2, open toward the outside, in the form of a cylindrical tang, with a smaller diameter than that of the body 1. In the inner surface of the head 2 a collar 5 is provided that protrudes radially inward.

A needle 10 is carried by a needle-carrier 11. The needle-carrier 11 comprises a cylindrical block 12 that has an axial hole to receive an end of the needle 10. Two flexible members 13 separated from each other by an axial slot 14 are connected to the cylindrical block 12. Each flexible member 13 has an outward facing groove 15.

The needle-carrier 11 is inserted in the hole of the head 2 and the grooves 15 of the member 13 engage in the collar 5 of the head 2 so as to retain the needle-carrier. In order to prevent the needle 10 from being extracted, a retaining cap 16 having a frustoconical shape is mounted on the head 2. The cap 16 engages the head 2, the part of cylindrical block 12 that protrudes outward from the head, and a small portion of needle 10 near the cylindrical block 12.

Figure 5:
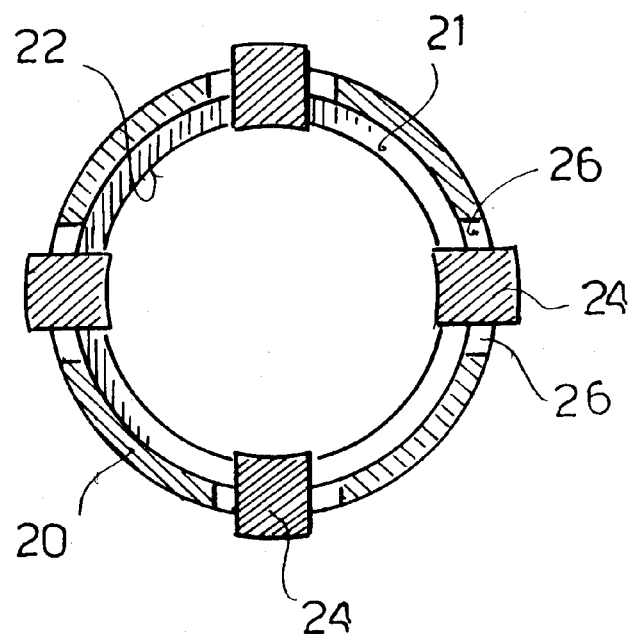
FIG. 5 is a cross sectional view of a sleeve member taken along the plane V—V of FIG. 1.

A cylindrical sleeve 20, hollow on the inside, having an outside diameter equal to or slightly-smaller than the inside diameter of the cylindrical body 1, has a bottom or end wall 21 in which a large circular hole 22- is formed, so that the bottom wall 21 forms an annular inward-facing projection. As shown in FIG. 5, at the opposite end to the bottom wall 21, the sleeve 20 has four flexible tongues 23, each defined by two longitudinal slots 26, so as to be able to bend inwardly and outwardly. Each tongue 23 ends in a tooth 24 having a tapered part 27 protruding inward, which ends with a radial abutment surface 25.

By outwardly parting the tongues 23, a coil spring 30 is inserted axially into the sleeve 20. The spring 30 is kept under compression with its ends abutting respectively against the bottom wall 21 and against the abutment surface 25 of the tooth 24.

The sleeve 20 is inserted from the rear opening of the syringe body 1, until its bottom wall 21 abuts against the projection 4 of the syringe body. In this position an end part of the tongues 23 protrudes axially out of the syringe body 1.

For simplicity of construction a sleeve 20 has been illustrated separate from the syringe body 1. However, the sleeve 20 can be formed in a single body with the syringe body 1. That is to say, the flexible tongues 23 can be formed at the rear end of the syringe body 1 and the spring 30 is interposed between an abutment surface of the syringe body and the abutment surface 25 of the teeth 24 of the tongues 23.

A plunger 40 is made of plastic material and has such a shape as to be able to slide tightly inside the chamber of the syringe body 1. The plunger 40 has a cavity 41 able to receive in engagement a head 51 of a stem or piston 50.

The head 51 of the stem 50 has a first annular flange 52 which engages in an annular seat 42 of the cavity 41 and a second abutment flange 53 against which the base of the plunger 40 abuts. At the end of the head 51 of the stem 50 is a blind tapered aperture 54, delimited at its open end by a collar 55 which protrudes inward.

As shown in FIG. 4, the stem 50 has an axial cylindrical part 56 from which four ribs 57 depart radially and extend substantially for the entire length of the stem 50. The rear end of the stem 50 has a circular flange 58 disposed transversally, with an annular protruding part 59 which provides a tapered outer lateral surface 60 and a straight inner lateral surface 61 defining a gap 62 with the end of the ribs 57 of the stem 50.

Operation of the syringe according to the invention is described hereunder.

In an initial situation the needle 10 is mounted on the head 2 of the syringe body 1, with the collar 5 of the head of the syringe body engaged in the grooves 15 of the members 13 of the needle-carrier 11. The sleeve 20 is mounted in the syringe body, with the teeth 24 of the tongues protruding from the rear end of the syringe body. The plunger 40 is situated inside the chamber of the syringe body, mounted on the head of the stem 50.

Initially the needle is positioned in the liquid to be drawn, and the user retracts the stem 50. The consequent retraction of the plunger 40 causes a depression in the chamber of the syringe body 1 thus the liquid is drawn into the chamber of the syringe body 1 through the needle 10.

When the injection is carried out, the user applies pressure to the flange 58 of the stem 50 causing an advancement of the plunger 40 which thus pushes the liquid which is injected through the needle 10.

As shown in FIG. 2, when the plunger 40 reaches the end of its stroke, the members 13 of the needle-carrier 11 enter the tapered cavity 54 of the head 51 of the stem 50.

Consequently the members 13 undergo an inward bending, and their grooves 15 disengage from the collar 5 of the head of the syringe body. At the same time, the grooves 15 engage in the collar 55 of the end of the head 50 of the stem. In this manner the head of the stem retains the needle-carrier 11.

When the plunger 40 is at the end of its stroke, the tapered surface 60 of the protruding annular part 59 of the end flange 58 of the stem begins to encounter the tapered surface 27 of the teeth 24 of the tongues 23 of the sleeve 20. Consequently the tongues 23 of the sleeve bend outward, thus the abutment surface 25 of the teeth 24 no longer retain the end of the spring 30 which is released, passing through the gaps 62 between the stem 50 and the protruding part 59 of the end flange 58 and abuts against the end flange 58, pushing it in the direction of retraction of the stem 50.

As shown in FIG. 3, since the needle-carrier 11 is constrained to the head 51 of the stem 50, when the spring 30 causes retraction of the stem, the needle 10 is drawn by the needle-carrier into the chamber of the syringe body 1. In this manner the syringe cannot be used for a further injection and does not allow accidental stabs, since the needle remains protected inside the chamber of the syringe body.

Moreover, according to per se known solutions which therefore are not illustrated, the grooves 15 of the members 13 of the needle-carrier can have profiles with a different shape to allow bending of the needle-carrier with respect to the axis of the syringe body. In this manner the needle 10 is no longer in axis with the syringe body and cannot accidentally protrude through the hole in the head 2 of the syringe body.

The present embodiment of the invention has been described with reference to a solution in which the needle-carrier is mounted inside the head of the syringe body so as to be captured by the plunger.

However, other solutions can be provided, such as for example the use of a needle-carrier mounted integrally with the plunger. In this case the head of the syringe body has sealing means to prevent leakage of the liquid from the annular gap formed between the outer surface of the needle and the inner surface of the head of the cylindrical body. Moreover, at least one channel which places the inner passageway of the needle in communication with the chamber of the syringe body will be provided in the needle-carrier or in the plunger.

a non-safety solution can also be provided in which the needle remains permanently mounted on the head of the syringe body.

Numerous variations and changes of detail within the reach of a person skilled in the art can be made to the present embodiment of the invention without thereby departing from the scope of the invention, set forth in the appended claims.

What is claimed is:

1. A disposable syringe comprising:
   a syringe body hollow on an inside and open at a front end and at a rear end thereof;
   a plunger which is slidable inside the syringe body having an injection stroke extending from a retracted syringe filling position to an advanced syringe emptying position, said plunger being provided at a rear thereof with a manually drivable stem driven out of the syringe body though the rear end thereof, and
   an injection needle integral with a needle-carrier that can be engaged to the front end of the syringe body or the plunger, wherein associated with said syringe body, retaining means able to retain spring means under compression are provided and, integrally with said stem, engagement means able to cooperate with said retaining means to free said spring means, when said plunger has reached an end of the injection stroke, are provided, so that said spring means can act on said stem to cause retraction thereof into the retracted position and retraction of the needle into the syringe body, said stem extending through the spring means;
   wherein said retaining means comprise flexible retaining tongues protruding axially form the rear end of the syringe body and said spring means are interposed between a first spring-bearing wall protruding radially from the inner surface of the syringe body and a second spring-bearing protection or surface protruding radially from the inner surface of said retaining tongues, said engagement means causing outward bending of said retaining tongues so as to free one end of said spring means retained by said second spring-bearing protection.

2. The syringe of claim 1, wherein said retaining tongues have an inwardly tapered surface at their end, terminating in said second spring-bearing projection.

3. The syringe of claim 1, wherein said retaining means comprise a cylindrical sleeve hollow on the inside and open at its ends, able to be inserted in the rear end of said syringe body, said first spring-bearing projection being obtained from the bottom wall of the sleeve, said retaining tongues being obtained by means of a plurality of axial notches in the sleeve open at the opposite end to the bottom wall, said bottom wall having a hole able to allow the passage of said stem.

4. The syringe of claim 4, wherein said syringe body has an abutment projection which protrudes radially from its inner surface, to lock said sleeve, in such a position that the end of the tongues protrudes outward from the rear end of the syringe body.

5. The syringe of claim 4, wherein said engagement means comprise a plate disposed at the rear end of said stem, said plate having an annular projection which protrudes axially and forward therefrom around said stem, said annular projection being able to cooperate with said retaining tongues to cause outward bending thereof.

6. The syringe of claim 1, wherein said engagement means comprise a plate disposed at the rear end of said stem, said plate having an annular projection which protrudes axially and forward therefrom around said stem, said annular projection being able to cooperate with said retaining tongues to cause outward bending thereof.

7. The syringe of claim 6, wherein between the inner surface of said annular projection and the outer surface of the rear end of the stem a gap is left, such as to allow the passage of said spring means so that the end of said spring means, when it is freed from said second spring-bearing projection, can abut against the inside surface of said end plate of the stem and the action of the spring means can cause retraction of the stem.

8. The syringe of claim 7, wherein the outer surface of said annular projection is tapered to cooperate with the inner tapered surface of said retaining tongues.

9. The syringe of claim 1, wherein said needle-carrier is mounted inside the head of the syringe body with its rear end inside the chamber of the syringe body, the plunger having a through hole which receives the head of said stem, the head of the stem having a blind hole with engagement means able to engage with the rear end of said needle-carrier so as to retain it to allow the needle to be pulled inside the chamber of the syringe body, during retraction of said stem.

10. The syringe of claim 9, wherein at the rear end of said needle-carrier are flexible members with grooves able to engage in a first collar provided in the inner surface of the head of the syringe body and said engagement means are a collar provided on the blind hole of the fore end of the stem, able to bend said members inward and engage the grooves of said members.

11. The syringe of claim 1, wherein said needle-carrier is mounted inside the head of the syringe body with its rear end inside the chamber of the syringe body, the plunger having a through hole which receives the head of said stem, the head of the stem having a blind hole with engagement means able to engage with the rear end of said needle-carrier so as to retain it to allow the needle to be pulled inside the chamber of the syringe body, during retraction of said stem.

12. The syringe of claim 11, wherein at the rear end of said needle-carrier are flexible members with grooves able to engage in a first collar provided in the inner surface of the head of the syringe body and said engagement means are a collar provided on the blind hole of the fore end of the stem, able to bend said members inward and engage the grooves of said members.

13. The syringe of claim 12, wherein said grooves have different profiles so that the needle-carrier is retained by the collar in a bent position with respect to the axis of the syringe body.

14. The syringe of claim 1, wherein said needle-carrier is mounted integrally on the plunger.

15. The syringe of claim 14 wherein sealing means are provided in said head of the syringe body to prevent leakage of liquid from the gap formed between the outer surface of the needle and the inner surface of the head and in that in said needle-carrier or in said plunger at least one channel is provided to put the inner passageway of the needle in communication with the chamber of the cylindrical body.

* * * * *

UNITED STATES PATENT AND TRADEMARK OFFICE
CERTIFICATE OF CORRECTION

PATENT NO.     : 6,716,191 B2
DATED          : April 6, 2004
INVENTOR(S)    : Sergio Restelli It is certified that error appears in the above-identified patent and that said Letters Patent is hereby corrected as shown below:

<u>Title page,</u>
Item [75], Inventor, "Rest Elli Sergio" should be -- Sergio Restelli --

Signed and Sealed this

Twelfth Day of October, 2004

JON W. DUDAS
*Director of the United States Patent and Trademark Office*